United States Patent [19]

Heyda et al.

[11] 4,366,820
[45] Jan. 4, 1983

[54] COMPOSING A REFERENCE HEART BEAT SIGNAL

[75] Inventors: Donald W. Heyda, Cambridge; Richard P. Corley, Sudbury, both of Mass.; Rosalind Sinclair, Nashua, N.H.

[73] Assignee: Baird Corporation, Bedford, Mass.

[21] Appl. No.: 162,301

[22] Filed: Jun. 23, 1980

[51] Int. Cl.³ .............................................. A61B 5/00
[52] U.S. Cl. .................................................. 128/659
[58] Field of Search ............................... 128/653, 659

[56] References Cited

U.S. PATENT DOCUMENTS

| | | | |
|---|---|---|---|
| 3,087,487 | 4/1963 | Cuynes | 128/731 |
| 4,033,335 | 7/1977 | Nickles | 128/659 |
| 4,197,836 | 4/1980 | Wagner et al. | 128/659 |
| 4,240,446 | 12/1980 | Groch et al. | 128/659 |

Primary Examiner—William E. Kamm
Attorney, Agent, or Firm—Morse, Altman, Oates & Dacey

[57] ABSTRACT

A method and apparatus for composing a reference heart beat by synchonously summing heart beat signals detected by a high resolution radioactivity distribution detection system for non-invasive measurement of cardiac performance. A plurality of sensing devices form an array for detecting radioactive events emitted from a heart under study. A processor sums heart beat images of a continuous series of detected events and generates a reference heart beat by synchronizing the regrouping of the beat images as a function of the peaks at volumetric end diastole and the image troughs at volumetric end systole. The reference heart beat represents a statistical standard heart beat for the heart under study and defines a base signal for quantative measurements and qualitative analysis of the condition of the subject heart.

7 Claims, 2 Drawing Figures

COMPOSING A REFERENCE HEART BEAT SIGNAL

BACKGROUND OF THE INVENTION

1. Field of the Invention

The present invention relates to nuclear medicine and, more particularly, is directed towards nuclear cardiology.

2. Description of the Prior Art

Electrocardiograph machines monitor electrical signals given off by the muscles of the heart as they pump blood around the body. These electrical signals, in combination with signals generated by a radioactivity distribution detection system, form a basis for non-invasive measurements of cardiac performance. A spike or R-wave in the signal monitored by the electrocardiograph is used to define the beginning of each heart beat. A series of measurements taken on a plurality of heart beats are added to provide sufficient statistical basis for valid cardiac diagnosis. Such non-invasive nuclear cardiac measurement techniques are costly and time consuming in that they require, in addition to a radiation detection apparatus, an electrocardiograph machine and the placement of associates electrodes on the body. Erratic electrical signals generated by the heart muscles and monitored by the electrocardiograph result in confusing diagnostic measurements.

SUMMARY OF THE INVENTION

A primary object of the invention is to provide a method and apparatus for composing a reference heart beat with which an actual heart beat can be compared for diagnostic purposes. Radioactive events emitted from a heart under study following administration of a diagnostic amount of a radioactive substance are sensed by a plurality of sensing devices that form an array. A processor synchronously sums and averages a series of heart beat image signals that are produced from a continuous series of sensed events and generates a reference heart beat. The processor synchronously regroups the heart beat image signals as a function of the maximum and minimum points of each heart beat cycle, the maximum and minimum points occurring at the ends of diastole and systole movements, respectfully. The reference heart beat, which defines a standard heart beat of the subject under study, provides sufficient statistical basis for quantative measurements and qualitative analysis of cardiac condition.

Other objects of the present invention will in part be obvious and will in part appear hereinafter.

The invention accordingly comprises the apparatuses processes, together with their parts, steps, elements and interrelationships that are exemplified in the following disclosure, the scope of which will be indicated in the appended claims.

BRIEF DESCRIPTION OF THE DRAWINGS

A fuller understanding of the nature and objects of the present invention will become apparent upon consideration of the following detailed description taken in connection with the accompanying drawings, wherein.

DETAILED DESCRIPTION OF THE PREFERRED EMBODIMENTS

Figure 1:
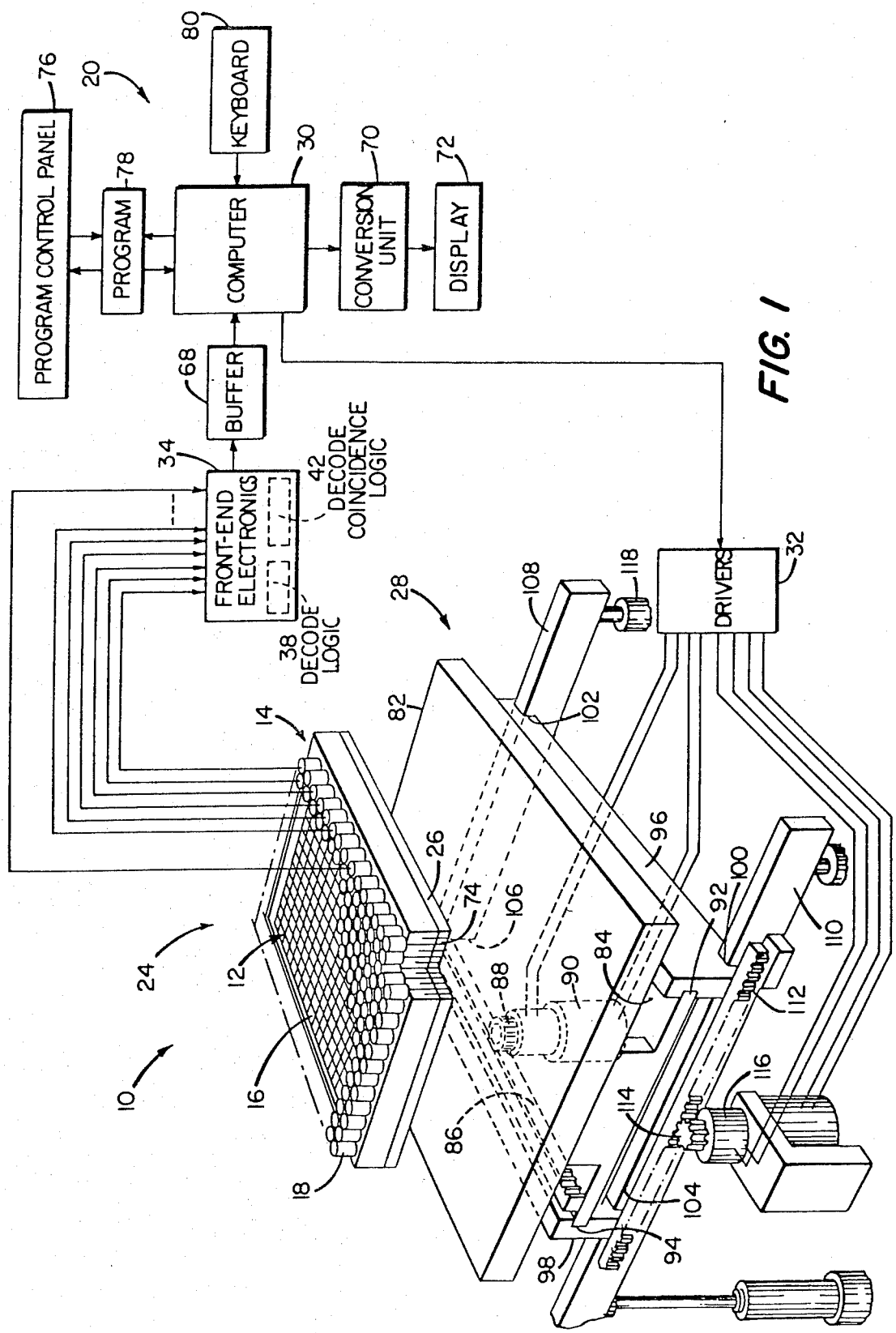
FIG. 1 is a block and schematic diagram of a high resolution radioactivity distribution detection system embodying the present invention.

Referred now to the drawings, FIG. 1 shows a radioactivity distribution detection system 10 for non-invasive measurements of cardiac performance of a biological specimen following administration of a diagnostic amount of a radioactive material by composing a reference heart beat that defines a statistical base for such measurements. System 10 includes a plurality of crystal assemblies 12 disposed in an array 14 for sensing radioactive events emitted from a heart under study and a processor 20 for generating data signals defining cardiac condition. Processor 20 generates the reference heart beat signal by synchronously summing a series of heart beat image signals produced from a continuous series of sensed events. The heart beat image signals are summed as a function of the maxima and minima for each heart beat image, the maxima and minima occurring at the ends of diastole and systole movements, respectively. The reference heart beat signal defines a standard heart beat of the subject under study, and provides sufficient statistical basis for quantative measurements and qualitative analysis of cardiac condition. That is, the reference heart beat signal is a data base for subsequent measurements and analysis.

Each crystal assembly 12 has four scintillators 16, each scintillator is at a unique address location in array 14 and, when activated by sensing radioactivity, emits a light signal. The light emitted by any one scintillator 16 is detected by a plurality of detectors 18, for example photomultiplier tubes, that are superimposed on crystal assemblies 12. A unique set of photomultiplier tubes 18 is disposed over one scintillator 16 in each of four adjacent crystal assemblies 12. Data signals generated by a photomultiplier tube 18 monitoring an activated scintillator 16 in a particular crystal assembly 12 and the photomultiplier tubes monitoring the adjacent scintillators of the particular crystal assembly are processed in processor 20 to provide a presentation of cardiac condition.

In the illustrated embodiment, radioactivity distribution system 10 includes a detector assembly 24 having a collimator 26, array 14 of crystal assemblies 12, and photomultiplier tubes 18. By way of example, collimator 26 is a multi-plane focused collimator characterized by at least two different focal lengths. A subject under diagnosis (not shown) is positioned on a programmable XY platform 28 that is in spaced relationship to detector 24. Equilibration of an injected radioactively tagged tracer in a blood pool is used as a reference beacon to position array 14 over the precordium. Command signals generated by a computer 30 in response to sensing of the tracer in the blood pool actuate a driver control 32 which operates to move platform 28 to the desired position. Individual scintillation events in detector assembly 24 are sensed and the coordinate position of each event is determined.

Array 14 is mounted in spaced registration with collimator 26 which includes a plurality of tapered collimator bores 74. Each scintillator 16 is disposed in registration with one taped collimator bore 74. Each collimator bore 74 is used to limit the field of view of each scintillator 16 to a unique spatial segment of the specimen being diagnosed. In this manner, a two dimensional image of the heart under diagnosis is obtained. The two dimensional image is made up of a specified number of picture elements that correspond to the number of unique spatial segments isolated by multi-bore collimator 26. The shape and volume of each separate spatial segment in the specimen is defined by the geometry of each collimator bore 74. A description of the detailed electronic circuitry for providing an image of the organ under diagnosis is found in U.S. Pat. Nos. 4,044,332 and 4,048,501, which are incorporated herein by reference.

Each scintillator 16 in array 14 has a unique address that is identified by a particular row and column location. Generally, one photomultiplier tube 18 is associated with four scintillators, one scintillator in each of four crystal assemblies 12 in adjacent rows and columns. One photomultiplier tube 18 is associated with two scintillators 16 at the edges of array 14 and one photomultiplier tube 18 is associated with one scintillator 16 at the corners of array 14. Data signals generated by photomultipliers 18 are processed in front-end electronics 34 which includes a decode logic unit 38 and a decode coincidence logic unit 42. The data signals at the outputs of photomultipliers 18 are decoded in decode logic 38. In addition, the signals at the outputs of photomultipliers 18 are applied to decode coincidence logic unit 42 which provides an indication that data signals have been detected from at least three adjacent photomultipliers.

The structure of each crystal assembly 12 is such that light from one scintillator 16 is coupled to four photomultiplier tubes 18. That is, most of the light from a scintillation in one scintillator 16 location in one crystal assembly 12 is sensed by one photomultiplier tube 18 that is superimposed on the activated scintillator. A smaller amount of light from the activated scintillator 16 is sensed by the two photomultiplier tubes 18 which are superimposed on the two scintillators that are adjacent the activated scintillator in the same crystal assembly 12. An even lesser amount of light from the activated scintillator 16 is sensed by the one photomultiplier tube 18 which is superimposed on the remaining scintillator 16 in the same crystal assembly. In this way, three photomultiplier tubes 18 determine the position of the activated scintillator 16 by the light emitted therefrom by pulse height weighting.

All acceptable data sensed by scintillators 16 in array 14 is accumulated and stored in a buffer memory 68. The XY address of each scintillator 16 is determined by the output signals generated by corresponding photomultiplier tubes 18 associated therewith. In memory 68, each sensed scintillator 16 event is accumulated to previously sensed events having the same address location. The number of events stored at a given address is the number of recorded disintegrations having originated within the monitored subject at a point, the XY location of which corresponds to the given address. Following the accumulation period, the accumulated data in raw digital form is fed to computer 30 and stored in corresponding address locations. The data in computer 30 in normalized into Gray scale coded signals as a function of the greatest number of detected events at any one address and fed to a halftone conversion unit 70. Signals generated by halftone conversion unit 70 are applied to a display 72 for controlling the number of dot picture elements per unit area at the XY display locations that correspond to the address locations.

As previously indicated, sensed events at each unique address are accumulated in memory 68. That is, the number of scintillation events for each XY location in array 14 is accumulated in a corresponding XY location in memory 68. Upon completion of the accumulation step, the data accumulated in memory 68 is fed to computer 30, memory 68 is cleared and is readied for reception of new data. The events accumulated during one accumulation period represents one heart beat image, and a series of accumulated events defines a series of heart beat images. Operation of the system is directed from a control panel 76 having a series of interconnected switching devices that are connected to computer 30 via a programmer 78. A manual data input 80, for example a keyboard, is provided for logging any pertinent data in a display 72.

Programmable XY platform 28 comprises a table 82 that is mounted to a slidable member 84. A rack, 86 which engages a pinion 88 of a driver 90, is mounted to member 84. Member 84 is slidably received in guideways 92, 94 that are provided in parallel guides 96, 98, respectively, rack 86 being in parallel spaced relationship with guides 96, 98. Guideway 92 extends along the longitudinal axis of guide 96 and guideway 94 extends along the longitudinal axis of guide 98. Guides 96 and 98 are formed also with a pair of transverse guideways 100, 102 and 104 and 104, 106, respectively. Guideway 100 is in registration with guideway 104 and guideway 102 is in registration with guideway 106. Fixed guides 108 and 110 are slidably received in guideways 100, 102 and 104, 106, respectively. Fixed guides 108 and 110 are in parallel spaced relationship to one another and in perpendicular spaced relationship with guides 96, 98. A rack 112, which engages a pinion 114 or a driver 116, is mounted to guides 96, 98 in parallel spaced relationship with guides 108, 110. It will be realized from the foregoing description that table 82, member 84 and rack 86 are slidable in a first direction within guideways 92, 94; and guides 96, 98 and rack 112 are slidable in a second direction within guideways 100, 102 and 104, 106; the first and second directions being mutually perpendicular to one another. For convenience, by way of example, the first and second directions will be referred to as the X and Y directions, respectively. That is, driver 90 moves table 82 in the X direction and driver 116 moves table 82 in the Y direction. Drivers 90 and 116, for example stepping motors, are controlled by signals generated by driver control 32 in response to command signals from computer 30. It is to be understood that platform 28 is movable also in the Z axis by means of jack screws 118, for example.

Figure 2:
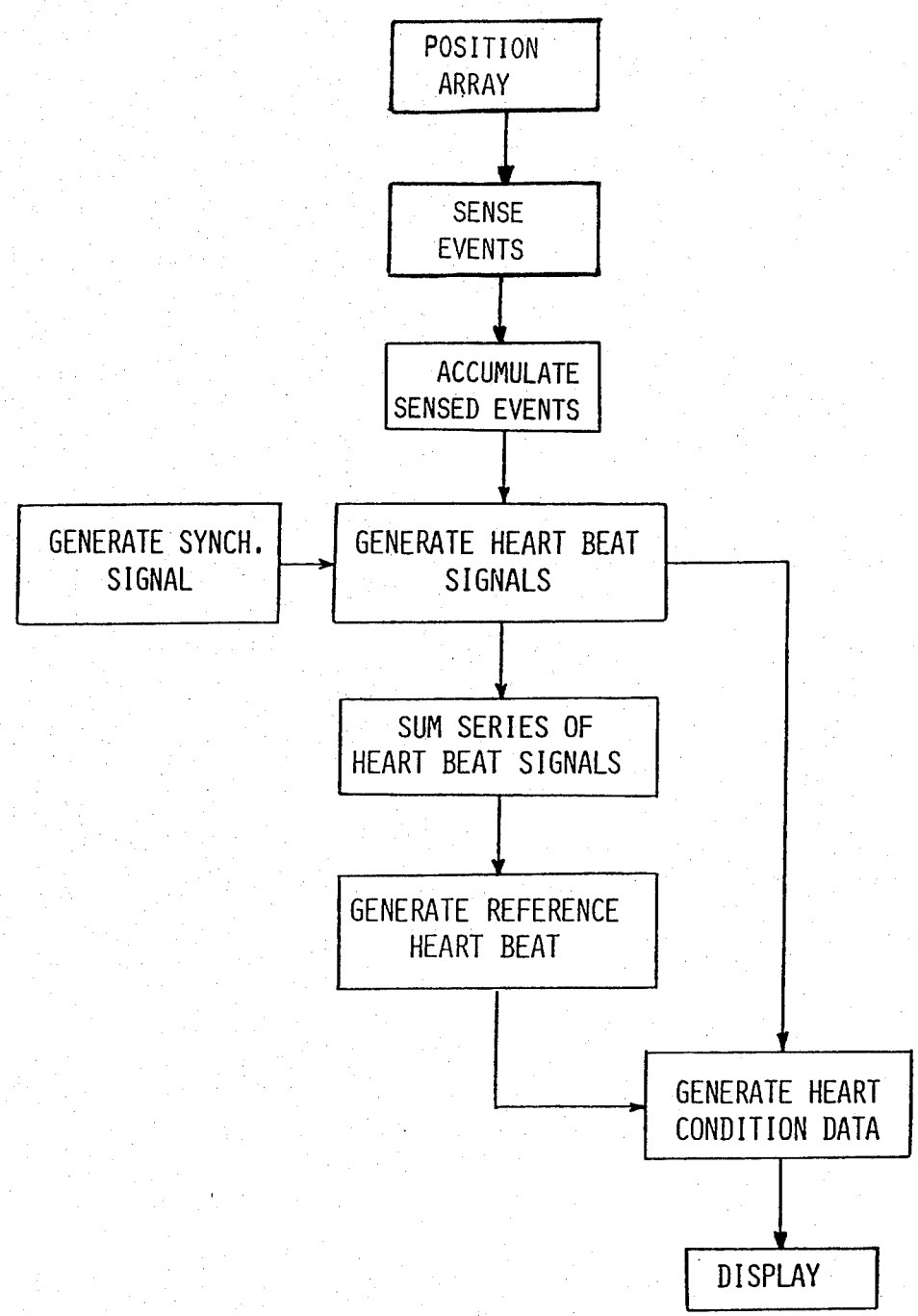
FIG. 2 is a schematic diagram illustrating certain principles of the invention.

As previously indicated, the precordial region of the subject under diagnosis is positioned under array 14 by moving platform 28. The desired location of the subject with respect to array 14 is determined by the blood pool containing the radioactively tagged tracer that is equilibrated in the blood without leaking into the intravascular spaces. As shown schematically in FIG. 2, after the step of positioning the subject is completed, a continuous series of events are detected by scintillators 16 and accumulated in memory 68 to events having the same XY locations in array 14. The series of detected events represents a continuous series of heart beat images or frames of heart beats. In the illustrated embodiment, by way of example, the continuous series of frames is detected for a period of ninety seconds at a rate of twenty frames per second. The eighteen hundred frames obtained during the ninety second period are synchronously averaged in processor 20 to provide a standard heart beat image which defines a data base for measurement and analysis of cardiac performance.

In the preferred embodiment, a region of array 14, which is positioned over either the left and/or right ventricle, is isolated in memory 68. Processor 20 generates a histogram of the sensed events which represents the number of counts over the isolated area versus time. Since the events are sensed while in a state of equilibrium, fluctuations in the number of counts are proportional to fluctuations in the blood pool and correspond to a volumetric measurement. Therefore, the points of successive maxima and minima count levels delineate the cardiac profile at end diastole and end systole, respectively. In the illustrative embodiment, maxima and minima are defined as the points where the first derivative changes sign with a magnitude greater than that of two standard deviations of statistical noise.

The standard of reference heart beat, which is a representative equilibrium heart beat, with increased statistics, but intact temporal resolution, is obtained by synchronously summing the image heart beats in processor 20 using the volumetric maxima and minima. Arrhythmic heart beats, which are determined from analysis of the periodicity of the beats, are included or excluded from the synchronous summation of beats that provides the representative equilibrium heart beat. The representative beat is composed from a contiguous set of images that describe an average beat of the heart. Using the representative heart beat as a statistical base, processor 20 generates data signals defining a quantative measurement of the heart function, for example, ejection fraction, ventricular volume curve, or regurgitant fraction. These data signals are based upon the proportionality of scintillation counts to the blood volume they perfuse. Also, processor 20 generates data signals defining qualitative assessments of heart wall motion. Such assessments are derived from an endless loop cinematic video display of the equilibrium representative cycle images.

Since certain changes may be made in the foregoing disclosure without departing from the scope of the invention herein involved, it is intended that all matter contained in the above description and depicted in the accompanying drawings be construed in an illustrative and not in a limiting sense.

What is claimed is:

1. A method for composing a reference heart beat signal of a subject under diagnosis, said method comprising the steps of:
   (a) sensing a series of radioactive events emitted from a heart under diagnosis at various address locations to provide representations thereof;
   (b) accumulating said representations of said events in a memory for a plurality of accumulation periods, said representations of said events being accumulated in certain address locations for each of said accumulation periods, certain of said accumulated representations of said events defining one heart beat image signal; and
   (c) synchronously regrouping a series of such heart beat image signals as a function of volumetric maxima and minima and averaging said series of such heart beat image signals to define a reference heart beat.

2. The method as claimed in claim 1 including the steps of positioning the heart of a subject under diagnosis and sensing means in relative alignment; and sensing said series of events while in an equilibrated state, the heart and sensing means positioning specified by an equilibrated radioactive tracer in a blood pool within the subject.

3. The method as claimed in claim 2 including sensing said equilibrated events as a function of maxima and minima count levels that define cardiac profile at end diastole and end systole, respectively.

4. A method for composing a reference heart beat signal of a subject under diagnosis, said method comprising the steps of:
   (a) positioning the heart of a subject under diagnosis for access by a detector means, said detector means operative to sense radioactivity;
   (b) sensing a series of radioactive events emitted from said heart to provide a series of representations;
   (c) accumulating said series of representations of sensed events at particular address locations in a memory for a plurality of accumulation periods, said representations of sensed events being accumulated at specific address locations for a specific accumulation period, said series of representations of events stored during each said accumulation period defining one heart beat image signal; and
   (d) synchronously regrouping a series of such heart beat image signals as a function of volumetric maxima and minima and averaging said series of heart beat image signals, to define a reference heart beat.

5. The method as claimed in claim 4 including sensing equilibrated events a function of maxima and minima count levels which occur at end diastole and end systole, respectively.

6. A system for composing a reference heart beat signal of a subject under diagnosis comprising:
   (a) sensing means,
   (b) means for positioning the subject under diagnosis for access by said sensing means, said sensing means sensing a series of radioactive events emitted from the heart of the subject under diagnosis;
   (c) memory means operatively connected to said sensing means for accumulating said sensed events for a plurality of accumulation periods, said events accumulated to sensed events having identical address locations for each accumulation period, said accumulated events defining one heart beat image signal; and
   (d) processor means operatively connected to said memory means for synchronously averaging a series of said heart beat image signals, said averaged heart beat image signals defining a reference heart beat, said processor containing means for synchronously regrouping said heart beat image signals as a function of volumetric maxima and minima of said heart.

7. The system as claimed in claim 6 wherein said processor contains means for synchronously regrouping said heart beat image signals as a function of corresponding points in each of said heart beat image signals.

* * * * *